United States Patent [19]

Longmire et al.

[11] Patent Number: 4,921,952

[45] Date of Patent: May 1, 1990

[54] NUCLEIC ACID ISOLATION PROCESS

[75] Inventors: Jonathan L. Longmire, Los Alamos, N. Mex.; Annette K. Lewis, La Jolla, Calif.; Carl E. Hildebrand, Los Alamos, N. Mex.

[73] Assignee: The United States of America as represented by the United States Department of Energy, Washington, D.C.

[21] Appl. No.: 341,281

[22] Filed: Apr. 20, 1989

Related U.S. Application Data

[63] Continuation of Ser. No. 146,557, Jan. 21, 1988, abandoned.

[51] Int. Cl.$^5$ .................... C07H 21/00; C07H 21/02; C07H 21/04
[52] U.S. Cl. ...................... 536/27; 536/28; 536/29; 536/127; 435/803
[58] Field of Search .................. 536/27-29, 536/127

[56] References Cited

PUBLICATIONS

Manintis et al., "Molecular Cloning, Abstrating Manual", Cold Spring Nebraska Laboratory, 1982, pp. 80-83.
Maniatis et al., "Molecular Cloning, a Laboratory Manual", Cold Spring Harbor laboratory, 1982, pp. 93-94.
Schlieg et al., "Practical Methods in Molecular Biology", Spring Verlag, New York, 1981, pp. 64-65.
Longmier et al., Nucleic Acids Research, vol. 15(2), pp. 859-860 (1987).
J. L. Longmire et al., "A Rapid and Simple Method for the Isolation of High Molecular Weight Cellular and Chromosome-Specific DNA in Solution Without the use of Organic Solvents", Nucleic Acids Research, 15, No. 2, p. 859 (1987).

*Primary Examiner*—Johnnie R. Brown
*Assistant Examiner*—L. Eric Crane
*Attorney, Agent, or Firm*—Ray G. WIlson; Paul D. Gaetjens; William R. Moser

[57] ABSTRACT

A method is provided for isolating DNA from eukaryotic cell and flow sorted chromosomes. When DNA is removed from chromosome and cell structure, detergent and proteolytic digestion products remain with the DNA. These products can be removed with organic extraction, but the process steps associated with organic extraction reduce the size of DNA fragments available for experimental use. The present process removes the waste products by dialyzing a solution containing the DNA against a solution containing polyethylene glycol (PEG). The waste products dialyze into the PEG leaving isolated DNA. The remaining DNA has been prepared with fragments containing more than 160 kb. The isolated DNA has been used in conventional protocols without affect on the protocol.

5 Claims, No Drawings

NUCLEIC ACID ISOLATION PROCESS

BACKGROUND OF THE INVENTION

This invention relates to isolating nucleic acid and, more particularly, to isolating high molecular weight DNA to obtain relatively long DNA fragments. This invention is the result of a contract with the Department of Energy (Contract No. W-7405-ENG-36).

This is a continuation of application Ser. No. 07/146,557 filed 01/21/88, now abandoned.

The isolation of high molecular weight DNA in solution is an essential step in molecular genetic studies of eukaryotic systems. The size and purity of isolated genomic or chromosome-specific DNA can greatly affect the ability to obtain optimal and reproducible results in a number of experimental applications, such as consistant restriction endonuclease digestions, construction of overlapping lambda or cosmid genomic libraries, and restriction-fragment detection by filter hybridization.

Although a number of modifications have been applied to conventional procedures for DNA purification in solution, all present protocols involve extractions using organic solvents. While organic extraction efficiently removes undesirable contaminants (i.e., detergents and proteins) from nucleic acid preparations, the multiple tube rotations and pipettings associated with these steps lead to a dramatic reduction of DNA size due to hydrodynammic shearing.

Organically extracted genomic DNA samples often contain fragments smaller than 23 kb in length. DNA sheared to this extent can result in decreased sensitivity in filter hybridization experiments, as well as reduced cloning efficiencies. Shear-induced size reduction is especially detrimental when isolated genomic DNA is to be partially digested to produce restriction fragments that are to be cloned into large insert accepting vectors, such as cosmids. Further, the inefficiency of DNA recovery through serial organic extractions complicates the isolation of very small masses of DNA.

These and other problems of the prior art are addressed by the present invention and an improved method is provided for isolating nucleic acid.

It is an object of the present invention to provide an efficient process for DNA isolation.

It is another object of the present invention to isolate DNA having relatively long fragments.

One other object of the present invention is to isolate DNA with minimum manipulation.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method of this invention may comprise isolating DNA from eukaryotic cell and flow sorted chromosomes to remove detergent and proteolytic digestion products. The solution containing the DNA is dialyzed against a solution containing polyethylene glycol (PEG) to obtain isolated DNA. The isolated DNA contains relatively long DNA fragments that are expected to facilitate molecular genetic studies which require the isolation of nucleic acids in solution.

DESCRIPTION OF THE INVENTION

In accordance with the present invention a rapid and simple DNA isolation procedure is provided in which the organic extraction steps of conventional protocols are replaced with dialysis against polyethylene glycol (PEG). PEG dialysis removes proteolytic digestion products and detergent contaminants and, because DNA solutions remain static during this process, shear-degradation is reduced. This novel procedure routinely yields high molecular weight DNA that can be restricted, ligated, and cloned with high efficiency. Since the DNA sample does not undergo serial transfers of an aqueous phase, efficiency of DNA recovery is enhanced and the purification of very small amounts of DNA becomes more practical. Additionally, this protocol can be used to obtain nondegraded cellular RNA.

EXAMPLE

Cell Culture

Cadmium sensitive Chinese hamster cell line CHO, and cadmium resistant (Cd) CHO variants 20F4 and 200T1 were grown in suspension culture in Ham F-10 medium (Flow Laboratories) supplemented with 15% heat-inactivated neonatal bovine serum (Biocell Laboratories). Cells to be analyzed for induction and synthesis of metallothionein (MT)-encoding RNA were cultured during exponential growth in the presence or absence of 100 $\mu$M $ZnCl_2$ for a period of four hours prior to harvest.

Polyethylene Glycol Isolation of Cellular Nucleic Acids

The following procedure has been performed with up to $3 \times 10^7$ diploid mammalian cells processed to yield up to approximately 200 $\mu$g of nuclear DNA:

1. Cells were harvested from suspension culture by centrifugation. Monolayers were harvested either by trypsinization or (if to be processed for RNA) by scraping. Harvested cells were washed twice by centrifugation and resuspension in ice cold calcium-free and magnesium-free phosphate buffered saline (CMF-PBS).

2. Washed cell pellets were resuspended within sterile 15 ml polypropylene tubes in 5.0 ml of autoclaved 10 mM Tris-HCl pH 8.0, 1 mM EDTA (TE buffer) at 22° C.

3. Stocks of 10% SDS (in autoclaved $H_2O$) and 10 mg per ml proteinase K (in autoclaved TE) were added to final concentrations of 0.1% and 100 $\mu$g per ml respectively. Tubes were inverted twice (to mix reagents) and the resulting viscous solutions were incubated at 37° C. overnight. In some instances Li acetate is added to a final concentration of 1M before the proteinase K to assist in stripping proteins off the DNA.

4. Using a Schleicher and Schuell UH020/2A microdialysis apparatus, each sample was dialyzed at 22° C., i.e., room temperature, against four 60 min. changes of 20% w/v PEG 8000 (Sigma) in TE (autoclaved). The PEG phase was slowly stirred during these steps. All microdialysis apparatus parts (except dialysis bags) and magnetic stir bars were autoclaved prior to use. Sample volumes were seen to decrease approximately 10-fold during PEG dialysis.

5. Desalting was accomplished by microdialysis against two 15–30 min. changes of autoclaved TE, also at 22° C.

6. Final processed samples were placed in sterile polypropylene tubes for long-term storage at 4° C.

Further Processing to Obtain Cellular RNA

1. Immediately following PEG dialysis and desalting, fresh PEG purified cellular nucleic acids were aliquoted into sterile 1.5 ml polypropylene tubes.

2. Autoclaved 1M $MgCl_2$ was added to give a final $Mg^{2+}$ concentration of 20 mM.

3. RNase-free RQ1 DNase (Promega Biotech) was then added at a two-fold unit excess.

4. Samples were mixed thoroughly and incubated at 37° C. for 20 min. Reactions were mixed a second time after the first 5 min. of incubation. A dramatic decrease in sample viscosity was observed following DNase treatment.

5. Immediately following incubation, SDS (in autoclaved $H_2O$) was added to a final concentration of 0.5%, and samples were then incubated 5 min. at 65° C.

6. Extraction was performed twice with chloroform:-phenol, once with chloroform, and samples were then precipitated in 0.3M Na-acetate and 2.5 volumes of absolute ethanol.

7. Following micro-centrifugation, RNA pellets were dissolved in a small volume of autoclaved TE containing 0.5% SDS. RNA solutions were then ready for spectrophotometric quantitation and subsequent manipulation (e.g., northern blot analysis).

DNA and RNA were prepared by the above process and were used in the following analytical procedures to demonstrate that PEG dialysis has no effect on clinical results:

1. restriction endonuclease digestion of PEG-isolated DNA;
2. electrophoresis blotting, and filter hybridization;
3. low percent gels;
4. conventional electrophoresis and blotting;
5. northern gel-blot analysis of PEG-isolated DNA;
6. hybridization of southern and northern blots to an Mt-specific probe; and
7. cloning of PEG-isolated chromosomal DNA.

The following results were obtained:

1. Purity of PEG-Isolated Nucleic Acids

Spectrophotometric absorbance data indicate that SDS-proteinase K treatment of eukaryotic cells followed by microdialysis against a 20% solution of PEG results in effective extraction of proteolytic products into the PEG phase leaving pure nucleic acids.

2. Size of PEG-Purified DNA

Due to the relative lack of shear-inducing steps, the size of PEG-prepared DNA is quite large. Aliquots of DNA were isolated (using the PEG method) from varying numbers of $Cd^r$ 200T1 cells and examined by low percent agarose gel electrophoresis. The size of DNA obtained was consistently equal to, or greater than, 160 kb.

3. Restriction of PEG-Isolated DNA

Aliquots (10 μg per reaction) of $Cd^r$ 200T1 DNA were digested with a variety of enzymes, followed by electrophoresis within a 0.8% agarose gel, Southern transfer, and hybridization to a $^{32}P$-labeled Mt-specific hamster cDNA probe. The resulting autoradiogram displayed characteristic MT-restriction patterns, demonstrating that PEG-prepared DNA is digestible in a reliable manner with a variety of restriction endonucleases. This indicates that SDS is concurrently removed, along with proteolytic products, during dialysis against 20% PEG.

4. Cloning of PEG-Isolated DNA from Flow Sorted Chromosomes

The number of plaque forming units (PFU) per microgram input DNA was observed for both conventionally purified chromosome specific DNA and PEG-isolated chromosomal DNA. The PEG-isolated DNA ligated and packaged with high efficiency to further confirm a lack of inhibitory contaminants within such preparations.

While the physical-chemical mechanisms of the PEG extraction are not fully understood, studies suggest that a surfactant-polymer interaction between SDS and PEG results in extraction of SDS into the polymer phase. The coincident removal of proteolytic digestion products may be related either to their free movement across the dialysis membrane, or to peptide-SDS interactions coupled with separation of SDS into the PEG phase.

These above results demonstrate that the PEG method eliminates the need for organic solvents in routine DNA isolations and may provide a more expedient approach to rapid batch purifications of DNA and RNA. The large size of DNA which can be consistently obtained using the PEG method is expected to increase cloning efficiency of partially digested DNA into large insert accepting bacteriophage and cosmid vectors. Additionally, due to its size, PEG-prepared DNA is expected to enhance the ability to detect large restriction fragments in filter hybridization experiments. Because of the simplicity, the PEG procedure lends itself well to potential automation. This procedure also promises to be useful in minimizing DNA losses during purification, an especially important consideration in cases in which only small amounts of DNA are available for manipulation. These advantages of the PEG extraction procedure will facilitate molecular genetic studies requiring the isolation of nucleic acids in solution.

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. In a process for preparing DNA from cellular materials for use in genetic studies of eukaryotic systems, a process for isolating DNA fragments from proteolytic digestion products and detergent products in a solution with said DNA fragments produced in stripping undesired cellular constituents from said DNA, wherein the improvement comprises the step of dialyzing a solution containing said DNA fragments, detergent products, and proteolytic digestion products against a solution containing PEG for a time effective to yield DNA sufficiently pure for said genetic studies.

2. A process according to claim 1, wherein said solution containing PEG is about 20% (w/v) PEG.

3. A process according to claim 1, further including the step of performing periodic changes of said PEG solution during said dialysis.

4. In a process for preparing DNA from cellular materials for use in genetic studies of eukaryotic systems, a process for isolating DNA fragments from proteolytic digestion products and detergent products in a solution with said DNA fragments produced in stripping undesired cellular constituents from said DNA, consisting essentially of dialyzing a solution containing said DNA fragments, detergent products, and proteolytic digestion products against a solution containing PEG.

5. A process according to claim 4, wherein said solution containing PEG is about 20% (w/v) PEG.

* * * * *